United States Patent [19]

Ghouri

[11] Patent Number: 5,380,305
[45] Date of Patent: Jan. 10, 1995

[54] HEMOSTATIC SAFETY CATHETER-CANNULA ASSEMBLY

[75] Inventor: Ahmed F. Ghouri, Des Moines, Iowa

[73] Assignee: Jerry D. Rockhold, Jr., Lineville, Iowa

[21] Appl. No.: 48,187

[22] Filed: Apr. 20, 1993

[51] Int. Cl.⁶ ............................................. A61M 5/00
[52] U.S. Cl. .................................. 604/263; 604/167; 604/236
[58] Field of Search ............... 604/193, 195, 198, 263, 604/162, 163, 192, 240, 136, 213, 215, 236, 164–169, 201, 205, 256; 137/355.18, 377, 382

[56] References Cited

U.S. PATENT DOCUMENTS

| | | | |
|---|---|---|---|
| 2,836,180 | 5/1958 | Strauss, Jr. | 604/164 |
| 3,159,159 | 12/1964 | Cohen | 128/766 |
| 4,190,048 | 2/1980 | Sampson | 604/175 |
| 4,243,034 | 1/1981 | Brandt | 604/169 |
| 5,062,836 | 11/1991 | Wendell | 604/167 |
| 5,098,394 | 3/1992 | Luther | 604/167 |

*Primary Examiner*—C. Fred Rosenbaum
*Assistant Examiner*—V. Alexander
*Attorney, Agent, or Firm*—G. Brian Pingel

[57] ABSTRACT

A hemostatic safety catheter-cannula assembly for the prevention of contamination by blood during vascular insertion includes a catheter-cannula having a flexible catheter-cannula tube connected to a base that includes a one-way valve member biased to normally prevent fluid flow through the catheter-cannula.

5 Claims, 2 Drawing Sheets

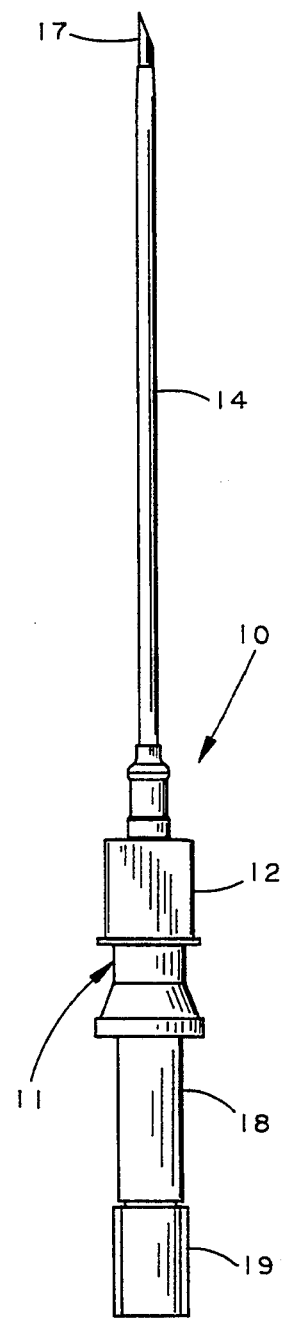
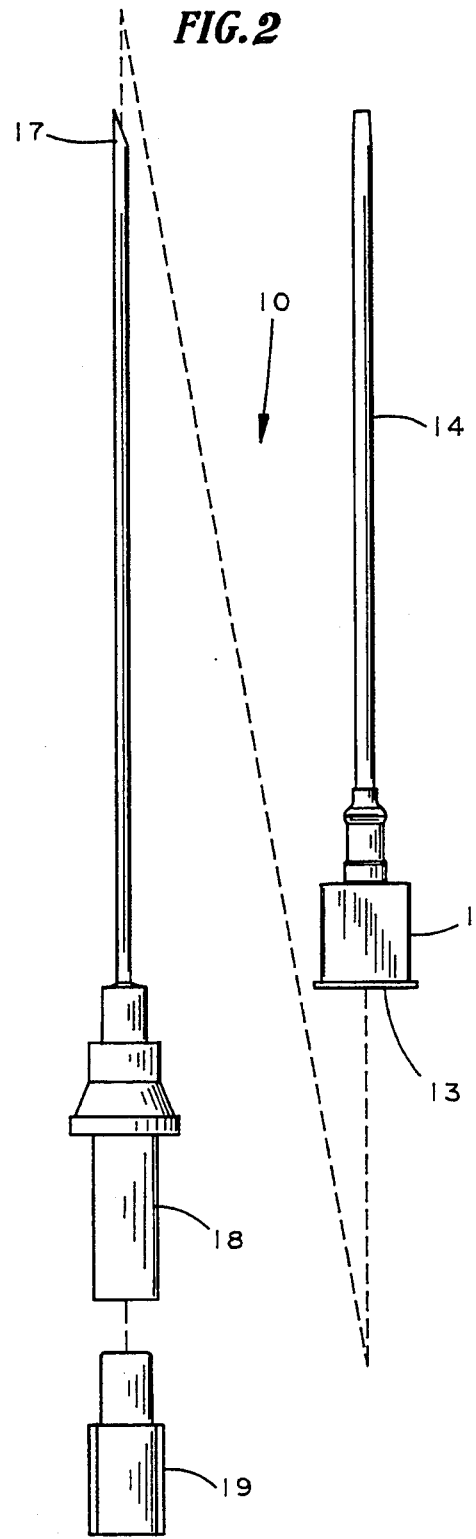
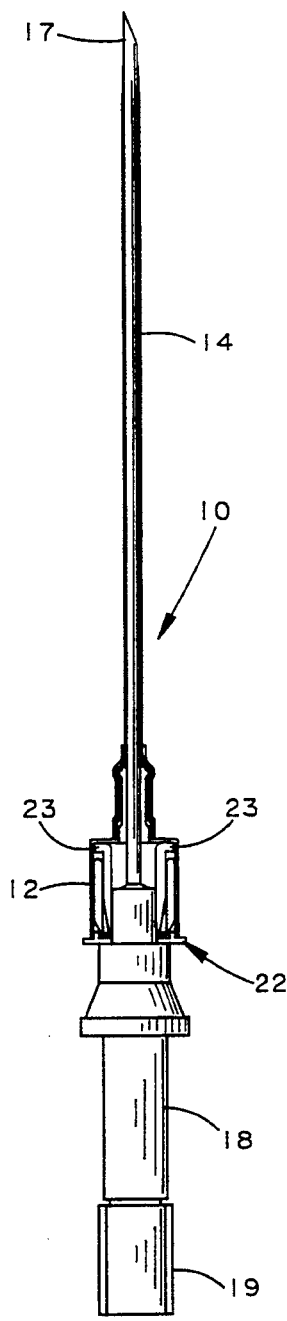

HEMOSTATIC SAFETY CATHETER-CANNULA ASSEMBLY

BACKGROUND OF THE INVENTION

1. Field of the Invention

The present invention relates in general to an intravenous or intra-arterial catheter-cannula assembly and more specifically concerns a catheter-cannula assembly that reduces the back flow of fluid through the assembly.

2. Description of the Prior Art

Intravenous and intra-arterial catheter-cannula assemblies are well-known in the prior art and are employed to deliver drugs, fluid or blood to a patient or for blood sampling. Such assemblies are utilized by insertion into a patient's vein or artery in combination with an introducer needle. Generally, the needle seats inside the catheter-cannula as a unit and is inserted into the patient's vein or artery. After the combined catheter-cannula and needle are properly positioned, the needle is then withdrawn and an intravenous infusion set or other appropriate device is connected to the end of the catheter-cannula for delivering fluid to the patient.

In making the infusion set hookup, there is often a problem of blood flowing through the catheter-cannula and out its hub end during the connection process, especially during arterial cannulation. In this age of deathly consequences resulting from contamination by blood-borne diseases, it is imperative that such back flow of blood through the catheter-cannula be avoided as much as possible.

Various types of devices have been developed for preventing the back flow of blood through the catheter-cannula. Most of the prior efforts, however, have been made by sealing the catheter-cannula with an elastomeric seal of some type or reseal plugs that allow penetration by a needle and are then resealable. Clamping devices have also been disclosed in the art that serve to provide a clamping of the catheter tubing as described in U.S. Pat. No. 4,198,973. Other devices for sealing the hub are the use of ball valve assemblies such as disclosed in U.S. Pat. No. 4,261,357. Various wing type cannula devices have also been proposed as indicated in U.S. Pat. No. 4,006,744.

None of the prior art devices described above have been fully satisfactory in preventing the back flow of blood and contamination when catheter-cannulas have been used. The present invention provides an improved method for achieving this objective and does so with a construction that is relatively simplistic and yet efficient.

SUMMARY OF THE INVENTION

A hemostatic safety catheter-cannula assembly for the prevention of contamination by blood during vascular insertion includes a catheter-cannula with a one-way valve means in the base of the catheter-cannula. The one-way valve means is biased to normally prevent blood flow through the catheter-cannula and is operable to open the one-way valve for blood flow by the end of fluid supply tubing inserted into the base of the catheter.

BRIEF DESCRIPTION OF THE DRAWINGS

FIG. 1 is a front view in elevation of a preferred embodiment of a catheter-cannula assembly of the present invention together with an insertion needle;

FIG. 2 is an exploded front view in elevation of the catheter-cannula assembly and insertion needle of FIG. 1;

FIG. 3 is a view similar to that of FIG. 1, but with the catheter-cannula in cross-section to show interior construction;

DETAILED DESCRIPTION OF THE PREFERRED EMBODIMENT

Figure 4:
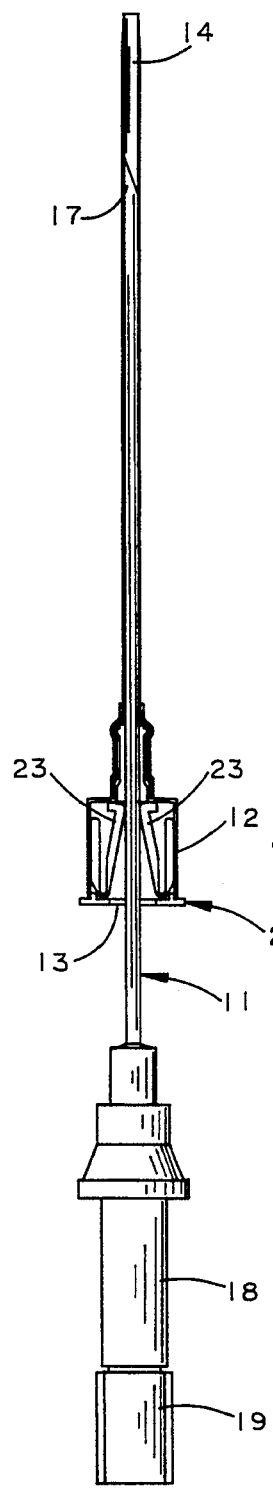
FIG. 4 is a view similar to that of FIG. 3, but with the insertion needle being partially retracted from the catheter-cannula assembly.

Referring to the drawings and more particularly to FIGS. 1, 2, and 3, a preferred embodiment of a hemostatic safety catheter-cannula assembly of the present invention is shown at 10 together with a trocar or insertion needle 11 slidably mounted within the catheter-cannula assembly. The assembly 10 is designed to be employed for purposes of reducing the back flow of blood and chance of contamination thereby.

The catheter-cannula assembly 10 includes a cylindrically shaped hollow base 12 that is open at its lower end 13 and is attached to a catheter-cannula tube 14 at its upper end. The tube 14 is preferably slender and smooth surfaced to provide minimal discomfort upon insertion in a patient. Also the tube is preferably formed of a flexible plastic material to reduce trauma to the patient. As shown in FIG. 1, the insertion needle 11 is slidably seated within the catheter-cannula assembly 10 and has its upper end 17 protruding outwardly from the upper end of said catheter-cannula assembly 10. The lower end portion 18 of the insertion needle 11 has a plug 19 slidably mounted within to block fluid flow therethrough. The plug 19 may include or be attached to a flash chamber to verify vascular entry.

Figure 5:
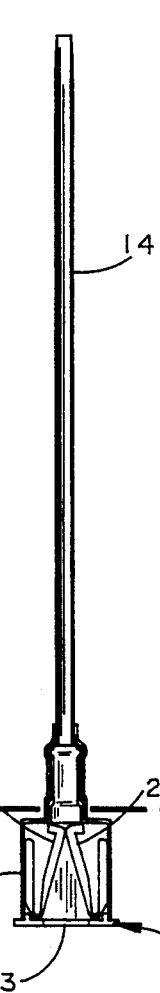
FIG. 5 is a cross-sectional front view in elevation of the catheter-cannula assembly of the preferred embodiment.
Figure 6:
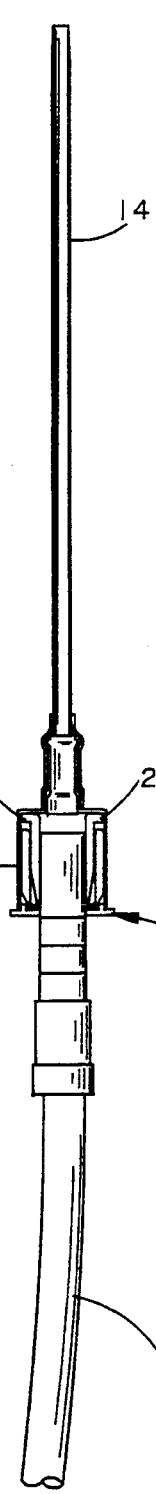
FIG. 6 is a front view in elevation of the assembly of FIG. 5 shown together with an intravenous tubing.
Figure 8:
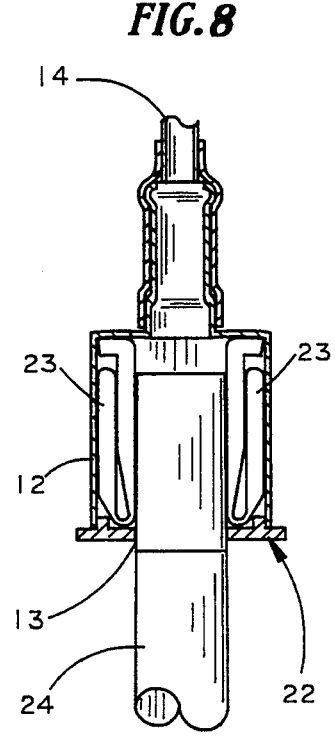
FIG. 8 is an enlarged cross-sectional view of the base of the catheter-cannula assembly shown in association with one end of an intravenous tubing.
Figure 7:
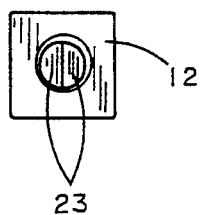
FIG. 7 is a cross-sectional view taken along the line 7—7 of FIG. 5.
Figure 9:
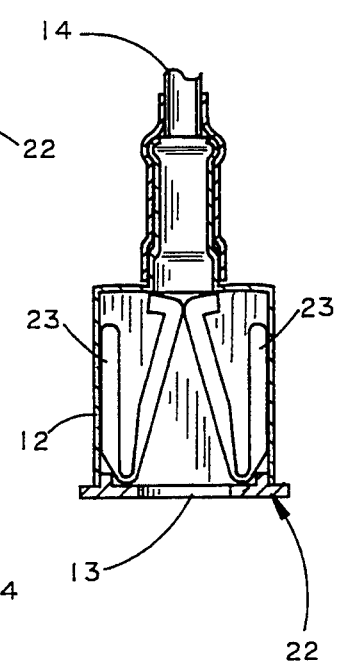
FIG. 9 is an enlarged view similar to that of FIG. 8 but with the intravenous tubing removed.

A one-way valve means 22 is mounted within the base 12 of the catheter-cannula assembly 10. The one-way valve means 22 comprises a pair of leaf springs 23 that are biased and rectangularly shaped at their upper ends, as shown in FIG. 7, to normally prevent blood flow through the catheter-cannula assembly 10, as shown in FIGS. 5, 7, and 9. The pair of leaf springs 23 serves as a gating means operable to open the one-way valve means 22 for blood flow by fluid supply tubing 24 into the base of the catheter-cannula, as shown in FIGS. 6 and 8. Preferably, the leaf springs 23 are formed from metal or other like material that is of a sufficient hardness and resilience so that movement of the needle 11 through the springs 23 does not abrade the springs and cause particles to break off therefrom. Furthermore, it precludes fixation of the springs 23 around the needle 11 during sterilization, as might occur if a soft substance were used to construct the valve means 22.

In the operation of the hemostatic safety catheter-cannula assembly 10 of the present invention, the trocar or insertion needle 11 is slidably seated within said catheter-cannula assembly. The outer end of the needle 11 protrudes outwardly from the upper end of the catheter-cannula assembly 10, and the plug 19 is slidably mounted in the lower end of the needle 11. A medical technician then inserts the needle 11 and catheter-cannula assembly 10 into the patient's vein, artery, or body cavity. The needle 11 is then drawn out of the catheter-cannula assembly 10.

During the sliding of the insertion needle 11 out of the catheter-cannula assembly 10, the one-way valve means 22 in the base 12 of the catheter-cannula assembly 10 engages the outer wall surface of the needle 11 until the end of the needle passes therethrough, as shown in FIG. 4. Thereupon, the pair of leaf springs 23 closes upon itself to seal the lower end of the catheter-cannula assembly 11 and thereby block the back flow of blood therethrough as shown in FIG. 5.

The catheter-cannula assembly 10 is then connectable to the conventional fluid supply tubing 24 as shown in FIG. 6, it being understood by those skilled in the art that fluid supply tubing will include a resilient end insertable through the self-sealing gating means to thereby reopen the catheter-cannula assembly 10 to the flow of fluid.

From the above description, it will be readily apparent to those skilled in the art that the present invention provides a safeguard, not provided heretofore in this automatic fashion, for medical personnel against exposure to infectious diseases when using catheter-cannula insertion needles.

It is to be understood that the form of the invention herewith shown and described is to be taken as a preferred example of the same, and that various changes in the shape, size and arrangement of parts may be resorted to, without departing from the spirit or scope of the invention.

I claim:

1. A hemostatic safety catheter assembly for the prevention of contamination by blood during vascular or intracavitary insertion, said assembly comprising:
   (a) a catheter including a base and a flexible catheter tube connected to the base;
   (b) a one-way valve means in the base of the catheter that is biased to normally prevent blood flow through the catheter and including a gating means operable to open the one-way valve means for fluid flow by fluid supply tubing that is inserted into the base of the catheter to engage and actuate the one-way valve; and
   (c) said one-way valve means is positioned in said base in such fashion that when said one-way valve means is opened by the insertion of said fluid supply tubing into the base, said gating means is moved into a position that does not disrupt the flow of fluid through said base so as to avoid turbulence in said fluid flow.

2. A catheter assembly according to claim 1 and further including a trocar or insertion needle slidably mounted within said catheter and having its distal end protruding outwardly from the distal end of said catheter.

3. A catheter assembly according to claim 1, wherein the gating means is formed of a material having a sufficient hardness and resilience so that it is not abraded by insertion of a trocar or needle into the base.

4. A catheter assembly according to claim 1 wherein said gating means is formed from a pair of spring type means.

5. A catheter assembly according to claim 1 wherein said gating means is formed from a pair of leaf springs.

* * * * *